United States Patent [19]

Thomas

[11] Patent Number: 5,107,835
[45] Date of Patent: Apr. 28, 1992

[54] ELECTROTHERAPEUTIC TREATMENT

[75] Inventor: Gary E. Thomas, Littleton, Colo.

[73] Assignee: Physiodynamics, Littleton, Colo.

[21] Appl. No.: 355,422

[22] Filed: May 22, 1989

[51] Int. Cl.$^5$ ............................................. A61N 1/00
[52] U.S. Cl. .................................. 128/419 R; 128/422
[58] Field of Search ............ 128/419 R, 419 D, 420.5, 128/421, 422

[56] References Cited

U.S. PATENT DOCUMENTS

| | | | |
|---|---|---|---|
| 2,532,788 | 12/1950 | Sarnoff | 128/421 |
| 2,771,554 | 11/1956 | Gratzl | 128/421 |
| 3,640,284 | 2/1972 | De Langis | 128/422 |
| 3,833,005 | 9/1974 | Wingrove | 128/422 |
| 3,908,669 | 9/1975 | Mau et al. | 128/422 |
| 4,019,519 | 4/1977 | Geerling | 128/422 |
| 4,071,033 | 1/1978 | Nawracaj et al. | 128/420 |
| 4,121,594 | 10/1978 | Miller et al. | 128/422 |
| 4,153,061 | 5/1979 | Nemec | 128/420 |
| 4,305,402 | 12/1981 | Katims | 128/741 |
| 4,374,524 | 2/1983 | Hedek et al. | 128/420 |
| 4,392,496 | 7/1983 | Stanton | 128/423 |
| 4,505,275 | 3/1985 | Chen | 128/421 |
| 4,535,777 | 8/1985 | Castel | 128/421 |
| 4,580,570 | 4/1986 | Sarrell et al. | 128/421 |
| 4,690,145 | 9/1987 | King-Smith et al. | 128/421 |
| 4,719,922 | 1/1988 | Padjen et al. | 128/421 |
| 4,763,656 | 8/1988 | Nauman | 128/421 |
| 4,850,357 | 7/1989 | Bach, Jr. | 128/419 D |

FOREIGN PATENT DOCUMENTS 773082  4/1957  United Kingdom ................ 128/419

OTHER PUBLICATIONS

D. Gilbert, *The Miracle Machine*, pp. 175-183 (1980).
G. Taubes, "An Electrifying Possibility", *Discover*, Apr. 1986, at 22-26 and 30-37.
J. Guyon, "New Wrinkle in Search for Youth", *The Wall Street Journal*, Mar. 22, 1989, at B1.

*Primary Examiner*—Frank S. Jaworski
*Assistant Examiner*—George Manuel
*Attorney, Agent, or Firm*—Sheridan, Ross & McIntosh

[57] ABSTRACT

The present invention involves a method of treating a patient by providing a signal that is exponential in character to the patient. The signal includes a relatively low-frequency, constant amplitude, periodic-exponential first component. Further, the signal preferably includes a relatively high-frequency, periodic-exponential second component.

33 Claims, 2 Drawing Sheets

ELECTROTHERAPEUTIC TREATMENT

FIELD OF THE INVENTION

The present invention relates to a method for treating a patient by providing electrical stimulation to the patient.

BACKGROUND OF THE INVENTION

Among the known types of apparatuses for applying an electrical stimulation to a patient is the interference type apparatus that is used to stimulate structures located within the patient's body, such as muscles and/or the nerves that control muscle action, that are reached with relatively high frequency signals, but are responsive to relatively low frequency signals. The interference apparatus operates by applying two primary signals of relatively high, but slightly different, frequencies to the patient's body. The primary signals, due to their relatively high frequency, penetrate the patient's body and reach the aforementioned structures where they intersect and produce a beat signal having a relatively low frequency that is equal to the slight difference in the frequencies of the primary signals. Exemplary of known interference type apparatuses is U.S. Pat. No. 4,374,524 to Hudek (1983) which illustrates the use of a square-wave signal generator in conjunction with a plurality of phase-locked loops and low-pass filters to produce a plurality of sine-wave, primary signals. Also representative of known interference type apparatuses are U.S. Pat. No. 4,071,033 to Nawracaj et al. (1978), and U.S Pat. No. 4,153,061 to Nemec (1979) which, in addition to providing two primary signals of different frequencies, also amplitude modulate the primary signals to achieve various therapeutic effects. For example, in Nawracaj two square-wave, primary signals are amplitude modulated by either a square-wave, ramp, exponential, semi-sine or sine-wave signal. In Nemec two sine-wave, primary signals are modulated by two low-frequency sine-wave signals to achieve stimulation at the point of application to the patient's body in addition to producing a beat signal therein.

Another known type of apparatus for applying an electrical stimulation to a patient's body is exemplified in U.S. Pat. No. 4,392,496 to Stenton (1983). Stenton applies two, apparently, square-wave signals to a patient's body in an alternating fashion to achieve muscle stimulation and prevent disuse atrophy. Further, in order to achieve optimal muscle stimulation and enhance the comfort of the patient, Stenton provides for the adjustment of several parameters associated with the applied signals, such as amplitude and frequency.

Yet another apparatus for administering an electrical stimulation to a patient's body is illustrated in U.S. Pat. No. 4,580,570 to Sarrell et al. (1986). The method of Sarrell is characterized by the application of pulses that have a relatively high voltage, high peak but low average current, and short duration. Moreover, the apparatus of Sarrell can be adjusted to apply the aforementioned pulses continuously, periodically, or in an alternating fashion.

Typically, the patient's body produces electrical signals, in the form of sensory and muscle nerve impulses, that are exponential in character. Characteristic, however, of the foregoing apparatuses is the application of signals, like sine-waves and square-waves, that are alien to the typical patient's body. Consequently, the patient can experience a certain amount of discomfort. Moreover, exposure to such alien signals can traumatize certain biological structures associated with the patient. Consequently, there exists a need for a method of electrotherapeutic treatment that produces a signal or signals that more closely resemble the exponential character of the patient's natural signals. There also exists a need for an electrotherapeutic method that produces a signal capable of penetrating the patient's body and that reduces any trauma imposed upon biological structures associated with the patient's body.

SUMMARY OF THE INVENTION

The present invention involves a method for relieving symptoms associated with injured tissue in a particular region of a patient. The method comprises providing a periodic-exponential signal in that region of the patient.

The present invention also involves a method for decreasing inflammation in an afflicted region in a patient by providing in the region a) a first periodic, double-exponential signal having a frequency between about 0 Hz and 1000 Hz and b) a second periodic, double-exponential signal having a frequency between about 1000 Hz and 100,000 Hz.

In another embodiment, the present invention involves a method for relieving symptoms associated with injured tissue in a region in a patient. The method comprises a) providing a first periodic-exponential signal; b) providing a second periodic-exponential signal; c) summing the first and second signals to produce a sum signal; and d) applying the sum signal to the region of the patient.

In a further embodiment the present invention involves a method for improving the relative strength of muscles associated with the eyeball. The method comprises providing a periodic-exponential signal to a selected group of the muscles.

In another embodiment, the present invention involves a method for treating an ulcer by providing a periodic exponential signal to the region of the patient containing the ulcer.

Another embodiment of the invention involves treating tissues infected with a virus by providing a periodic-exponential signal to the tissue.

A further embodiment of the instant invention involves blocking plasma kinins from receptor sites in a region in a patient by providing a periodic-exponential signal to the region.

DETAILED DESCRIPTION

Figure 1:
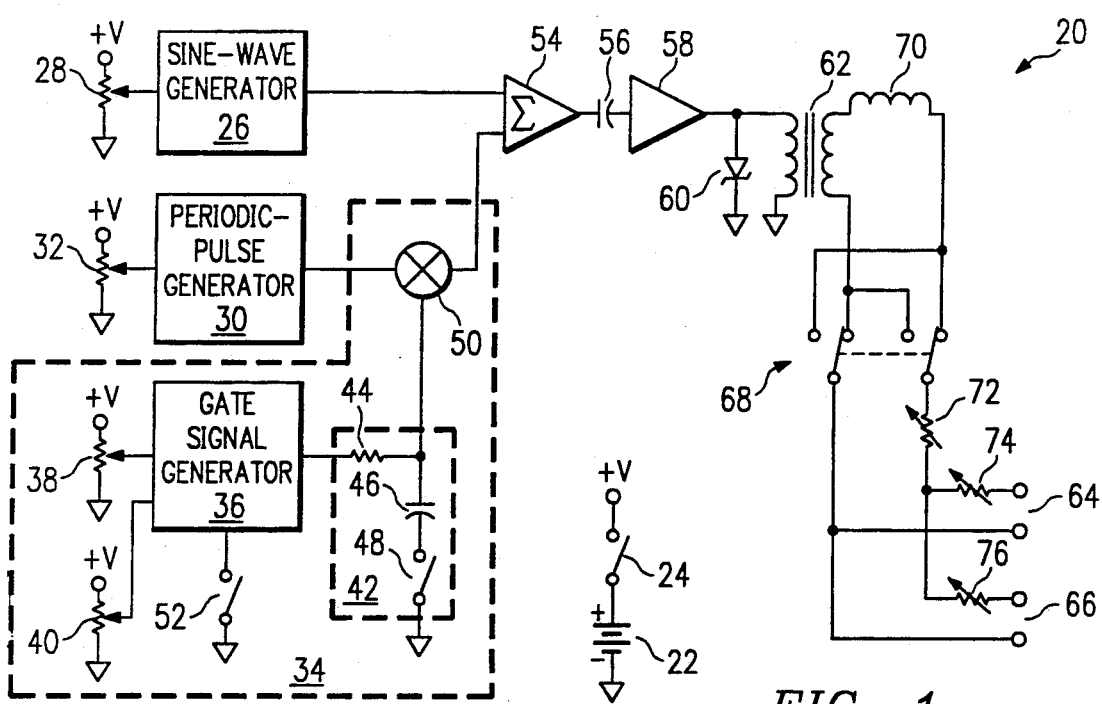
FIG. 1 illustrates a first embodiment of the apparatus useful in the invention.

With reference to FIG. 1, a first embodiment of an apparatus, useful in the practices of the instant method, the electrotherapeutic apparatus 20 (hereinafter referred to as the apparatus 20), is illustrated. The apparatus 20 generates a periodic-exponential signal that is applied to a patient in order to provide the desired treatment. The apparatus also, preferably, generates a periodic-exponential signal that causes sensory stimulation. The term patient as used herein includes vertebrate animals, such as humans, horses, cattle, dogs, cats, birds, snakes and the like.

The apparatus 20 includes a power supply 22, preferably a six-volt battery, for providing operating voltages to the remainder of the apparatus 20. A power supply switch 24 allows an operator to selectively turn "on" and "off" the apparatus 20 by, respectively, connecting and disconnecting the power supply 22 from the remainder of the apparatus 20.

The apparatus 20 further includes a sine-wave generator 26 for producing a constant amplitude sine-wave signal with a frequency of approximately 10-kHz. The 10-kHz sine-wave signal is within the frequency range that is typically used to stimulate the sensory nerves of a patient, i.e., in the range of about 1,000–100,000 Hz. If frequencies outside of this range are found to provide sensory stimulation to the patient, then the frequency of the sine-wave signal produced by the sine-wave generator 26 can be adusted accordingly. Adjustment of the amplitude of the sine-wave signal is, at least in part, achieved by a first rheostat 28. Preferably, the first rheostat 28 is adjusted when the apparatus 20 is manufactured and is thereafter inaccessible to an operator of the apparatus 20.

The apparatus 20 further includes a periodic-pulse generator 30 for producing a constant amplitude periodic-pulse signal with a frequency ranging from 40 Hz to 500 Hz. The frequency of the periodic-pulse signal encompasses the frequency spectrum that is generally used to stimulate the muscles of a patient, i.e. D.C. to 1,000 Hz. If frequencies outside of this range are found to provide muscle stimulation to the patient, then the frequency of the periodic-pulse signal produced by the periodic-pulse generator 30 can be adjusted accordingly. Adjustment of the frequency of the periodic-pulse signal is provided by a second rheostat 32.

Also included in the apparatus 20 is a gating means 34 for selectively gating the periodic-pulse signal produced by the periodic-pulse generator 30 in a periodic fashion. In other words, the gating means 34 operates to alternatingly allow and inhibit the passage of the stimulation periodic-pulse signal to the patient's body. The preferred gating means 34 includes a gating signal generator 36 for producing a periodic-pulse signal, hereinafter referred to as the gating signal. The period of the gating signal can be adjusted from approximately five seconds to one minute by a third rheostat 38. A fourth rheostat 40 allows the duty cycle of the gating signal to be adjusted from about five percent to about ninety-five percent. Further included in the preferred gating means 34 is a gradual on-off means 42 for selectively smoothing the rising and falling edges of the gating signal thereby producing the effect of gradually allowing and inhibiting the passage of the stimulation signal. The preferred gradual on/off means 42 includes a resistor 44 and a capacitor 46 which, when a first switch 48 is closed, act as a low-pass filter that smooths the rising and falling edges of the gating signal. The preferred gating means 34 further includes a multiplier 50 for alternatingly allowing and inhibiting the passage of the periodic-pulse signal output by the periodic-pulse generator 30 according to the gating signal. For example, if the gating signal is zero then the multiplier 50 inhibits the passage of the periodic-pulse signal. If, on the other hand, the gating signal is non-zero, then the multiplier 50 allows the periodic-pulse signal or a portion thereof to pass. Additionally, the preferred gating means 34 includes a second switch 52 for allowing an operator to selectively allow or inhibit the gating signal from reaching the multiplier 50. In other words, the second switch 52 gives the operator the option of using or not using the gating apparatus 34. Specifically, when the second switch 52 is open, the gating signal is applied to the multiplier 50 and the periodic-pulse signal is gated accordingly. When the second switch 52 is closed, the gating signal is not applied to the multiplier 50 and the multiplier 50 allows the periodic-pulse signal to pass unattenuated.

The apparatus 20 further includes a summing amplifier 54 for adding the sine-wave signal produced by the sine-wave generator 26 and the periodic-pulse signal output by the multiplier 50 to produce a sum signal. One cycle of the sum signal, less any DC component, includes a first portion and a second portion. The first portion reflects the sum of the sine-wave signal and the pulse portion of the periodic-pulse signal. The second portion reflects the sum of the sine-wave signal and the portion of the periodic-pulse signal when the pulse is absent. Since the periodic-pulse signal is zero when the pulse is absent, the second portion of the sum signal is, essentially, just the sine-wave signal.

Apparatus 20 further includes an AC coupling capacitor 56 and, a power amplifier 58 and a zener diode 60. The AC coupling capacitor 56 serves, at least in part, to eliminate any DC component in the sum signal output by the summing amplifier 54. The AC coupling capacitor 56 can be either a discrete component or the capacitance associated with the power amplifier 58 can be used. Similarly, the zener diode 60 can be either a discrete component or the breakdown characteristics of the power amplifier 58 can be employed. Preferably, the AC coupling capacitor 56 and the zener diode 60 are realized by using the capacitance and breakdown characteristics of the power amplifier 58, respectively. Consequently, the AC coupling capacitor 56 and zener diode 60 shown in FIG. 1 are representations of the capacitance and breakdown characteristics of the power amplifier 58. The operation of the capacitor 56, power amplifier 58 and zener diode 60 is now described during the first and second portions of a single cycle of the sum signal output by the summing amplifier 54. The first portion of the sum signal passes through the capacitor 56 to the power amplifier 58 where it drives the power amplifier 58 into the cutoff region. When the power amplifier 58 is in the cutoff region it does not output any current. The zener diode 60, however, cooperates with a transformer to maintain a defined voltage at the output of the power amplifier 58 for the duration of the first portion of the sum signal. Further, the zener diode 60 operates to blank out a substantial portion of the sine-wave signal aspect of the first portion of the sum signal. Consequently, a pulse having the defined voltage is produced at the output of the power amplifier 58 even though the power amplifier is operating in the cutoff region. In addition, while the power amplifier 58 is in cutoff, the bias voltage supplied by the power supply 22 charges the capacitor 56. The second portion of the sum signal is substantially unaffected by the operation of the zener diode 60. The capacitor 56 and the power amplifier 58 do, however, affect the second portion of the sum signal. Specifically, the capacitor 56 passes the second portion of the sum signal on to the power amplifier 58 and discharges the charge accumulated during the first portion of the sum signal into the power amplifier 58 in an exponential fashion. The discharging of the capacitor 56 results in the second portion of the sum signal being exponentially amplitude modulated. Once the capacitor 56 is completely discharged, exponential amplitude modulation of the second portion of the sum signal ceases and a constant amplitude steady state is attained. The second portion of the sum signal also drives the power amplifier into saturation during a portion of each cycle of the sine-wave signal that comprises the second portion of the sum signal. Consequently, the power amplifier 58 also clips a portion of each cycle of the sine-wave signal. In summary, the one cycle of the sum signal produced at the output of the power amplifier 58 includes a pulse, the first portion, and a clipped sine-wave signal that is, for a time, exponentially amplitude modulated the second portion.

The apparatus 20 also preferably includes a step-up transformer for increasing the voltage of the sum signal existing at the output of the power amplifier 58. In the preferred embodiment the step-up transformer is a 1:10 step-up transformer 62. The sum signal at the output of the step-up transformer 62 is, following further processing discussed hereinafter, distributed to means for applying it to the patient. In the embodiment illustrated in FIG. 1, the sum signal output by the step-up transformer 62 is, in the preferred embodiment, distributed to a first pair of pads 64 and a second pair of pads 66 that are applied to the patient's skin. Alternatively, the sum signal can be distributed to applicators, such as point applicators, that can be moved over the patient's skin during treatment. Other means for applying the sum signal to the patient include an internal applicator that is inserted into the body of the patient, such as a needle electrode, and a remote applicator, such as a transmission antenna.

A double-pole, double-throw switch 68 allows an operator to change the polarity of the sum signal applied to the first and second pairs of pads 64, 66.

The apparatus 20 further includes a shaping means that is used to exponentially shape the sum signal output the transformer 62 and applied to the patient by the first pair of pads 64 and/or the second pair of pads 66. With reference to a single cycle of the sum signal, exponential shaping results in the rising and/or falling aspects of the first portion of the sum signal including an exponential component. Exponential shaping also, preferably, results in the rising and/or falling aspects of each cycle of the sine-wave signal comprising the second portion of the sum signal including an exponential component. Preferably, the shaping means is used to impart a double-exponential character to the sum signal where both the rising and falling edges of the first portion of the sum signal and each cycle of the sine-wave signal in the second portion of the sum signal include an exponential component. Preferably, the shaping means includes an inductor-resistor network comprising an inductor 70, a fifth rheostat 72, a sixth rheostat 74 and a seventh rheostat 76. The inductor 70 can be either a discrete component or incorporated into the transformer 62. The inductor 70, the fifth rheostat 72, sixth rheostat 74, seventh rheostat 76 and the electrical load provided by the patient cooperate to exponentially shape the sum signal existing at the first pair of pads 64. While not wishing to be bound by theory, it is believed that the following explanation correctly models the interaction of the shaping means and the patient in exponentially shaping the sum signal produced at the first pair of pads 64. The inductor 70, fifth rheostat 72 and sixth rheostat 74 define, at least in part, the "L/R" exponential time constant that determines the exponential character of the sum signal applied to the patient by the first pair of pads 64. The electrical load provided by the patient also defines, at least in part, the "L/R" exponential time constant that determines the exponential character of the sum signal applied to the patient by the first pair of pads 64. Specifically, the inductor 70 defines the "L" portion of the exponential time constant and the fifth rheostat, sixth rheostat and resistance provided by the patient across the first pair of pads 64 determines the "R" portion of the exponential time constant. The resistance across the first pair of pads 64 is substantially infinite when they are not attached to a patient. Consequently, the exponential time constant approaches zero and the sum signal output by the transformer 62 is substantially unaffected. If, however, the first pair of pads 64 are attached to a patient, then a non-zero exponential time constant is established and the sum signal is shaped accordingly. Specifically, the patient establishes a finite resistance across the first pair of pads 64 which, in combination with inductor 70, fifth rheostat 72 and sixth rheostat 74, defines a non-zero exponential time constant. Consequently, the exponential character of the sum signal applied to the patient is defined in part by the resistance provided by the patient, i.e., the sum signal accommodates to the patient. The patient is roughly modeled as a resistance in series with a large capacitor. The "RC" exponential time constant associated with the patient is relatively large with respect to the aforementioned "L/R" time constant. Consequently, the capacitance associated with the patient is relatively insignificant and can be ignored for purposes of explaining the interaction between the patient and the shaping means. Adjustment of the fifth rheostat 72 and/or the sixth rheostat 74 alters the exponential time constant and, hence, the exponential character of the sum signal applied to the patient by the first pair of pads 64. In addition, adjustment of the fifth rheostat 72 and/or the sixth rheostat 74 affects the amplitude of the sum signal applied to the patient by the first pair of pads 64. The inductor 70, fifth rheostat 72 and seventh rheostat 76 operate in an identical fashion with respect to the sum signal applied to the patient by the second pair of pads 66. A shaping means that does not interact with the electrical load provided by the patient is also feasible.

Figure 2A:
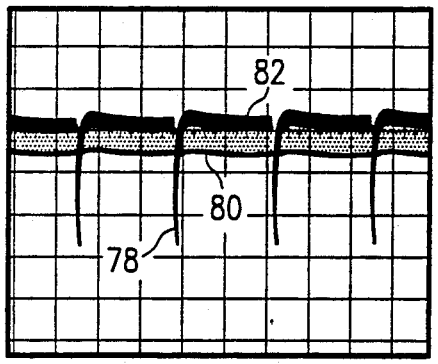
FIG. 2A illustrates several cycles of the sum signal that is applied to a patient's body by the apparatus shown in FIG. 1.
Figure 2B:
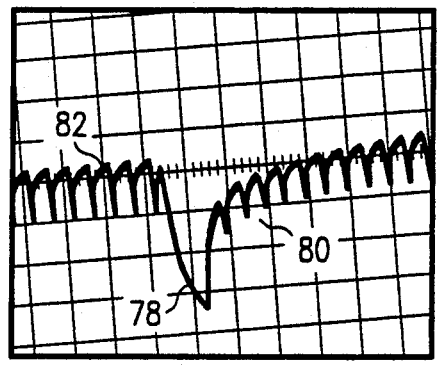
FIG. 2B illustrates a portion of a single cycle of the sum signal that is applied to a patient's body by the apparatus in FIG. 1.
Figure 2C:
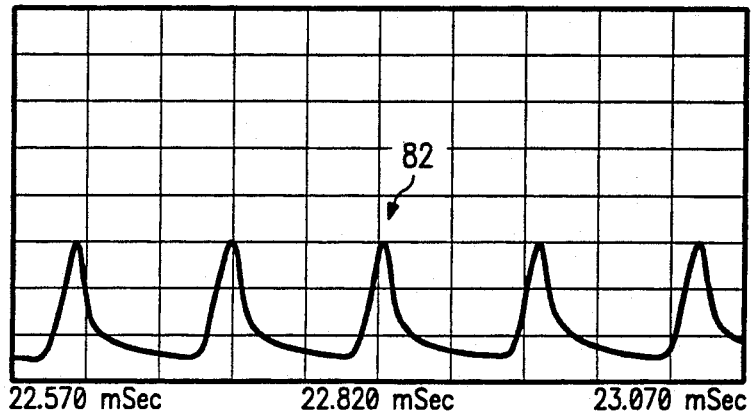
FIG. 2C illustrates the substantially constant amplitude periodic-exponential portion of the sum signal that is applied to a patient's body by the apparatus shown in FIG. 1.

FIGS. 2A and 2B illustrate the sum signal applied to a patient by either the first pair of pads 64 or the second pair of pads 66 with the double-pole, double-throw switch 68 in a first orientation. The sum signal includes a substantially constant amplitude, periodic-exponential portion 78 suitable for muscle stimulation. The sum signal also includes an exponentially amplitude modulated, clipped, periodic-exponential portion 80. As shown in FIGS. 2A–2C, the exponential amplitude modulation eventually terminates and a clipped, periodic- exponential signal 82 results. The clipped, periodic-exponential signal 82 shown in FIG. 2C was produced with the double-pole, double-throw switch 68 in a second orientation. Consequently, the clipped, periodic exponential signal 82 in FIG. 2C is the mirror image or opposite polarity of the corresponding clipped, periodic-exponential signals shown in FIGS. 2A and 2B.

Figure 3:
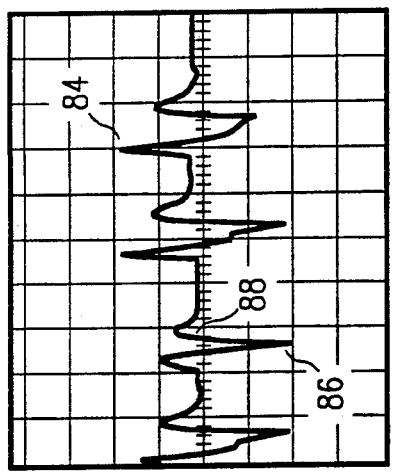
FIG. 3 shows the signal naturally produced by a human patient.

FIG. 3 shows a natural signal 84 produced by a human patient. The natural signal 84 includes a double-exponential portion 86 that corresponds to the constant amplitude, periodic-exponential signal 78 produced by the apparatus 20. The natural signal 84 also includes an exponentially amplitude modulated portion 88 that corresponds to the exponentially amplitude modulated, clipped, periodic-exponential signal produced by the apparatus 20. Consequently, the sum signal produced by the apparatus 20 corresponds, at least in part, to the signal 84 naturally produced by the human patient.

Operation of the apparatus 20 includes an initialization phase where the power supply switch 24 is placed in the "off" position to insure that when the pads are subsequently applied to the patient an undesirable signal is not also applied to the patient. Initialization also involves setting the fifth, sixth and seventh rheostats 72, 74, 76 for maximum attenuation to insure that the minimum amplitude sum signal is applied to the patient when the power supply switch 24 is closed. Further, the second rheostat 32 is set such that the periodic-pulse generator 30 will produce a periodic-pulse signal having a frequency at or about the mid-range of possible frequencies when the power supply switch 24 is closed. Also during initialization, the third and fourth rheostats 38, 40, are set such that when the power supply switch 24 is closed, a gating signal will be produced by the gate signal generator 36 that has a frequency in the mid-range of possible frequencies and a duty cycle of about fifty percent. During initialization, the second switch 52 is opened to insure that the gating signal is applied to the multiplier 50 when the power supply switch 24 is closed. Additionally, the first switch 48 is closed during initialization so that when the power supply switch 24 is closed the gating signal produced by the gate signal generator 36 is smoothed before application to the multiplier 50. Following initialization of the aforementioned switches and rheostats, the first pair of pads 64 and/or the second pair of pads 66 are attached to the patient's body at the points where muscle stimulation is desired. Preferably, treatment is effected along the longitudinal axis of the muscle. Preferably a pad is placed at each end of the muscle along the longitudinal axis of the muscle with the muscle itself between the pads with one pad preferably placed closer to the center of the body of the patient. If the muscle being treated is a frontal muscle, then the pad should be placed on the frontal part of the body. If a dorsal or posterior muscle is involved, then the pads should be placed on the dorsal part of the body. If it is not possible to treat the muscle along its longitudinal axis, then transverse treatment of the muscle can be effective. In this case, the pads are placed perpendicular to the longitudinal axis of the muscle being treated. Once the pads are attached to the patient, the power supply switch 24 is closed and the apparatus 20 generates the sum signal comprising the substantially constant amplitude, periodic-exponential signal 78 and the exponentially amplitude modulated, clipped, periodic-exponential signal 80. The sum signal is applied to the patient via the pads. Due to the aforementioned adjustment of the fifth, sixth and seventh rheostats 72, 74, 76 the sum signal applied to the patient is of minimum amplitude. At this point the exponential character and amplitude of the sum signal being applied to the patient can be adjusted using the fifth rheostat 72 and the sixth or seventh rheostats 74, 76. In addition, the frequency of the periodic-pulse portion of the sum signal can be adjusted using the second rheostat 32. Adjustment of the frequency and duty cycle of the gating signal can be accomplished by manipulating the third and fourth rheostats 38, 40. If the gating signal is not desired, then the second switch 52 can be closed.

Figure 4:
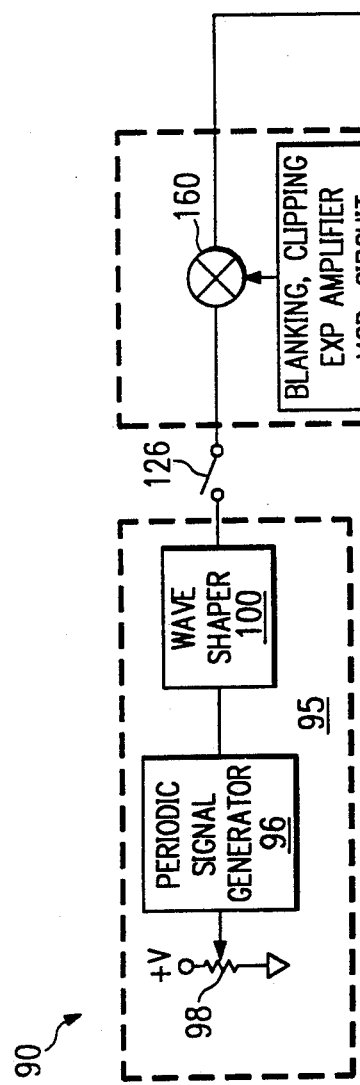
FIG. 4 illustrates a second apparatus useful in the invention.
Figure 4:
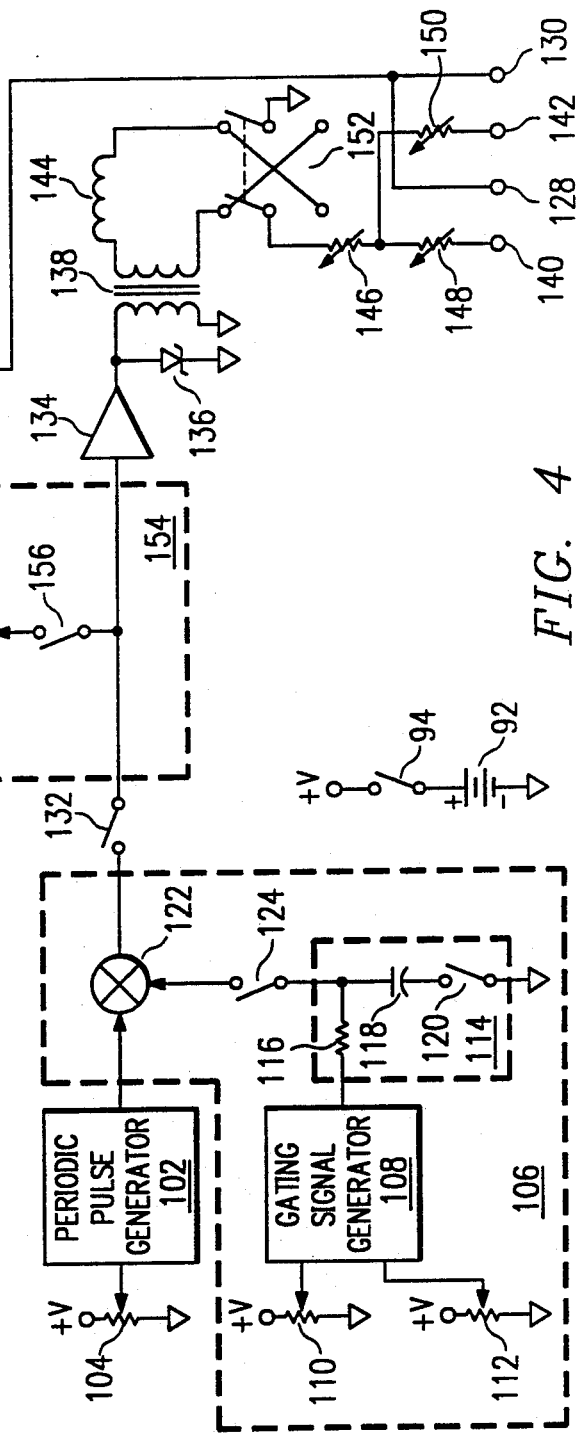

FIG. 4 illustrates a second embodiment of the invention, i.e., the electrotherapeutic apparatus 90 (hereinafter referred to as the apparatus 90). Apparatus 90, in contrast to apparatus 20, does not sum a sine-wave signal and a periodic-pulse signal. Rather, apparatus 90 applies the a periodic-exponential signal suitable for sensory stimulation and a periodic-exponential pulse signal suitable for muscle stimulation to the body of the patient over separate paths. The apparatus 90 allows an operator to control whether the periodic-exponential signal suitable for sensory stimulation, periodic-exponential pulse signal suitable for muscle stimulation or both signals are applied to the patient. The apparatus 90 also allows the operator to selectively blank, exponentially amplitude modulate, and clip the periodic-exponential signal used for sensory stimulation.

The apparatus 90 includes a power supply 92 and power supply switch 94 which operate in a substantially similar fashion to the power supply 22 and the power supply switch 24 of apparatus 20.

The apparatus 90 further includes a periodic-exponential signal generator 95 for producing a constant amplitude periodic-exponential signal having a frequency appropriate for stimulation of the sensory nerves of a patient. The preferred periodic-exponential signal generator 95 includes a periodic signal generator 96 for outputting a constant amplitude periodic signal. Preferably, the power associated with the periodic signal output by the periodic signal generator 96 is sufficient to penetrate the patient's body. Amplitude adjustment of the periodic signal output by the periodic signal generator 96 is provided by a first rheostat 98. Preferably, the first rheostat 98 is adjusted when the apparatus 90 is manufactured and is thereafter inaccessible. The periodic signal output by the periodic signal generator 96 can have virtually any shape since the preferred periodic-exponential generator 95 includes a wave-shaper 100 that is designed to modify the shape of whatever signal is being output by the periodic signal generator 96 to produce a constant amplitude periodic-exponential signal. For example, if the periodic signal generator 96 is outputting a constant amplitude square-wave signal, then the wave-shaper is designed to modify the square-wave shape to a periodic-exponential shape. Exponential shaping of the periodic signal output by the periodic signal generator results in the rising and/or falling aspects of the periodic signal having an exponential component. Preferably, the wave-shaper 100 imparts a double-exponential character to the periodic signal where both the rising and falling aspects have an exponential component.

The apparatus 90 further includes a periodic-pulse signal generator 102 for generating a periodic-pulse signal having a frequency suitable for muscle or motor stimulation of a patient. The frequency of the stimulation pulse signal output by the stimulation periodic-pulse signal generator 102 is adjusted by manipulating a second rheostat 104.

The apparatus 90 further includes a gating means 106 that alternatingly allows and inhibits the passage of the periodic-pulse signal. The preferred gating means 106 includes a gating signal generator 108 for producing a gating signal. The period and duty cycle of the gating signal produced by the gating signal generator 108 can be adjusted by, respectively, a third rheostat 110 and a fourth rheostat 112. A gradual on/off means 114, preferably comprising a resistor 116, a capacitor 118 and a first switch 120, provides an operator with the option of smoothing the rising and falling edges of the gate signal such that the periodic-pulse signal is gradually applied and then removed from the patient. A first multiplier 122 gates the periodic-pulse signal produced by the periodic-pulse signal generator 102 according to the gating signal. A second switch 124 provides an operator with the option of using or not using the gating apparatus 106.

The apparatus 90 further includes a third switch 126 that gives an operator with the option of providing or not providing the background periodic-exponential signal output by the wave-shaper 100 to a means for applying the signal to the patient. Specifically, if the third switch 126 is open then the periodic-exponential signal is not applied to the patient. When the third switch 126 is closed, the periodic-exponential signal is applied to the patient using one or more pads attached to the patient's skin. Preferably, a first pad 128 and a second pad 130 are employed to apply the periodic-exponential signal to the patient. Alternatively, the periodic-exponential can be applied to the patient's skin using a point applicator that can be moved over the patient's skin during treatment. Other means for applying the periodic-exponential signal to the patient include an internal applicator, such as a needle electrode inserted into the body of the patient, and a remote applicator, like a transmission antenna.

The apparatus 90 further includes a fourth switch 132 for providing an operator with the option of applying or not applying the periodic-pulse signal to the patient. Specifically, when the fourth switch 132 is open, the stimulation periodic-pulse signal is not applied to the patient. However, when the fourth switch 132 is closed, the periodic-pulse signal output by the first multiplier 122 is applied to a power amplifier 134 which amplifies the periodic-pulse signal. The amplified periodic-pulse signal is then applied to a regulator, which in the preferred embodiment is a zener diode 136. The zener diode 136 can be a discrete component or the breakdown characteristic of the power amplifier 134 can be employed. Once processed by the zener diode 136, the periodic-pulse signal is applied to a step-up transformer for increasing the voltage of the periodic-pulse signal. In the preferred embodiment of apparatus 90, a 1:10 step-up transformer 138 is used.

The periodic-pulse signal output by the transformer 138 is, following processing described more thoroughly hereinafter, distributed to means for applying it to the patient. In the embodiment illustrated in FIG. 4, the periodic-pulse signal is applied to a patient using one or more pads attached to the patient's skin. Preferably, a third pad 140 and a fourth pad 142 are used to apply the periodic-pulse signal to the patient. Alternatively, the periodic-pulse signal can be applied to the patient's skin using a point applicator that can be moved over the patient's skin during treatment. Other means for applying the periodic-pulse signal to the patient include a device inserted into the interior of the patient's body, like a needle electrode, and a remote applicator, like a transmission antenna.

The apparatus 90 further includes a shaping means that is used to exponentially shape the periodic-pulse signal output by the transformer 138 and applied to the patient by the third and fourth pads 140, 142. Exponential shaping of the periodic-pulse signal results in the rising and/or falling aspects of the pulse in the periodic-pulse signal include an exponential component. Preferably, the shaping means imparts a double-exponential character to the periodic-pulse signal where both the rising and falling of the pulse in each cycle of the periodic-pulse signal include an exponential component. Preferably, the shaping means includes an inductor-resistor network comprising an inductor 144, a fifth rheostat 146, a sixth rheostat 148, and a seventh rheostat 150. The inductor 144 can be either a discrete component or incorporated into the transformer 138. The inductor-resistor network operates, as previously discussed with respect to apparatus 20, to modify the periodic-pulse signal output by the transformer 138 such that the periodic-pulse signals applied to the patient by the third and fourth pads 140, 142, are constant amplitude periodic-exponential signals.

A double-pole, double throw switch 152 allows an operator to change the polarity of the constant amplitude periodic-exponential signals applied to the patient by the third and fourth pads 140, 142.

The apparatus 90 also includes a blanking, clipping and exponentially amplitude modulating circuit 154 for blanking the periodic-exponential signal output by the wave shaper 100 when a pulse associated with the periodic-exponential signal output by the multiplier 122 is present and clipping, together with exponentially amplitude modulating, the periodic-exponential signal otherwise. The blanking, clipping and exponentially amplitude modulating circuit 154 is comprised of a fifth switch 156, a blanking, clipping and exponential amplitude modulating signal generator 158 and a second multiplier 160. The blanking, clipping and exponential amplitude modulating circuit 154 operates such that when the fifth switch 156 is closed, the blanking, clipping and exponentially amplitude modulating signal generator 158 produces a signal that, upon application to the second multiplier 160, results in the periodic-exponential signal being blanked during the presence of a pulse associated with the periodic-exponential pulse signal. When the periodic-exponential signal is not blanked due to the presence of a pulse associated with the periodic-exponential pulse signal, it is clipped, and exponentially amplitude modulated.

With reference to FIGS. 2A-2C, the various signals that can be applied to the patient by manipulation of the third switch 126 and the fourth switch 132 are illustrated. When the third switch 126 is closed and the fourth switch 132 is open, a constant amplitude, periodic-exponential signal 82 having a frequency suitable for sensory stimulation is applied to the patient. When the third switch 126 is open and the fourth switch 132 is closed, a constant amplitude periodic-exponential signal 78 having a frequency suitable for muscle stimulation is applied to the patient. When both the third switch 126 and the fourth switch 132 are closed, both of the constant amplitude, periodic-exponential signal 78 and the periodic-exponential signal 82 are applied to the patient. Further, if both the third switch 126 and the fourth switch 132 are closed, then the fifth switch can be closed to blank, clip and exponentially amplitude modulate the periodic-exponential signal 82. Once the appropriate signal or signals have been selected then the operator can manipulate the rheostats to further modify the signal or signals being applied to the patient.

Operation of the apparatus 90 includes an initialization phase where the power supply switch 94 is placed in the "off" position to insure that when the pads are subsequently applied to the patient an undesirable signal is not also applied to the patient. Initialization also involved setting the fifth, sixth and seventh rheostats 146, 148, 150 for maximum attenuation to insure that the minimum amplitude periodic-exponential signal, if selected, is applied to the patient upon the closing of the power supply switch 94. Further, the second rheostat 104 is set such that the periodic-pulse generator 102 produces a periodic-pulse signal having a frequency at or about the mid-range of possible frequencies. Also during initialization the third and fourth rheostats 110, 112, are set such that upon the closing of the power supply switch 94 a gating signal is produced by the gate signal generator 108 that has a frequency in the mid-range of possible frequencies and a duty cycle of fifty percent. During initialization, the second switch 124 is closed to insure that the gating signal is applied to the multiplier 122 when the power supply switch 94 is closed. Additionally, the first switch 120 is closed during initialization so that when the power supply switch 94 is closed the gating signal produced by the gate signal generator 108 is smoothed before application to the multiplier 50. Also during initialization of the third switch 126, fourth switch 132 and fifth switch 156 are opened or closed depending upon what type of signal is desired. Following initialization of the aforementioned switches and rheostats, one or more of the pads are attached to the patient's body at the points where muscle stimulation is desired. Preferably, treatment is effected along the longitudinal axis of the muscle. Preferably a pad is placed at each end of the muscle along the longitudinal axis of the muscle with the muscle itself between the pads with one pad preferably placed closer to the center of the body of the patient. If the muscle being treated is a frontal muscle, then the pad should be placed on the frontal part of the body. If a dorsal or posterior muscle is involved, then the pads should be placed on the dorsal part of the body. If it is not possible to treat the muscle along its longitudinal axis, then transverse treatment of the muscle can be effective. In this case, the pads are placed perpendicular to the longitudinal axis of the muscle being treated. Once the pads are attached to the patient, the power supply switch 94 is closed and the desired signal is generated by the apparatus 90 and applied to the patient via the pads. Due to the aforementioned adjustment of the fifth, sixth and seventh rheostats 146, 148, 150 the periodic-pulse signal, if applied to the patient, is of a minimum amplitude. If the periodic-exponential pulse signal is applied to the patient, its amplitude can be adjusted using the fifth, sixth and seventh rheostats 146, 148, 150. In addition, the frequency of the periodic-exponential pulse can be adjusted using the second rheostat 104. Further, if the gating signal is being used, its frequency and duty cycle can be adjusted by manipulating the third and fourth rheostats 110, 112. If the gating signal is not desired, then the second switch 124 can be opened.

Application of the above-described periodic-exponential signal is particularly useful in the treatment of a number of afflictions of vertebrate animals. Generally in conducting the treatment, it is preferred to apply the signal at a power setting which is past the point of complete comfort to the patient but below the threshold of pain. The application of such a signal is useful in treating or relieving certain symptoms associated with injured tissue in a patient. The present process is also useful in treating certain problems of a patient by stimulating muscles. The instant method is advantageous in muscle stimulation compared to other electrotherapeutic treatments in that fewer treatments are required with this process.

The afflictions and symptoms which can be treated are believed to be associated in some way with tissue damage including without limitation: inflammation; contusion; edema; hematoma; ulcers; block plasma kinins in particular bradykinins and affecting viral diseases and insect and snake bites; arthritis symptoms; strains; and sprains. The instant method can advantageously decrease pain associated with a traumatic injury.

The present method can be particularly useful in reducing inflammation. The process can be used to treat gingivitis; treat tendinitis including, but not limited to the achilles, elbow and hand; treat contusions including but not limited to the ankle, arm, breast, buttock, collarbone, elbow (to include the ulnar nerve), face, foot, hand, kidney, knee, leg, thigh, and wrist; treat synovitis including but not limited to the ankle, knee and hip; treat tenosynovitis including but not limited to the ankle, knee, hip, arm, shoulder, foot, hand and wrist, and treat shin splits. The treatment can be used to reduce or eliminate trauma induced edema. The present method can also reduce or eliminate hematoma including that of the foot, leg, thigh, arm, and hand. The treatment can also induce regeneration of soft tissue, bone and nerves.

The instant process can be used to: treat certain ulcers, especially gastrointestinal ulcers including particularly peptic and gastric; intervene in viral diseases and decrease or inhibit the increase of virus, possibly by increasing the efficacy of the immune system; stimulate hair growth and regrowth; and initiate cell dedifferentiation and the resulting redifferentiation by unlocking repressed genes.

The present process can be used to: block plasma kinins, in particular bradykinins, from receptor sites; neutralize insect and arachnid bits; neutralize poisonous snake bites, both protoplasmic and neurological; and anesthetize locally and globally. The instant process can be useful in the alleviation of drug dependency.

The treatment using the instant signal can also be used to maintain and increase the range of motion of body limbs. It can be useful in the treatment of strains, including, but not limited to, ankle, achilles tendon, abdominal wall, arm, back (grades 1 and 2, lumbodorsal region), back (grades 1 and 2, sacroiliac region), back (grades 1 and 2, lumbar region), chest muscle, collar bone, elbow, foot, groin, hand, hip, knee, leg, thigh, wrist, and fingers. Sprains can also be treated, including but not limited to, ankle, arm, back (grades 1 and 2, lumbodorsal region), back (grades 1 and 2, sacroiliac region), back (grades 1 and 2, lumbar region), breast bone (sternum), chest muscle, elbow, foot, groin, hand, hip, jaw, knee, leg, thigh, wrist, thumb and fingers. Relief of bursitis can also be provided, including, but not limited to that of the elbow, foot, hip and knee. Treatment of elbow epicondylitis (tennis elbow) can also be provided. Symptoms associated with arthritis can also be treated, including Reiter's syndrome. Tendonitis, including that of the achilles, elbow and hand can also be treated.

The application of the above-described signal is useful in stimulating muscles. Afflictions and symptoms associated with muscle spasms or weakness can be treated with the instant process.

The application of such a signal is useful in promoting the relaxation of muscle spasms, for example, the relaxation of muscle cramps, the treatment of menstrual cramps and the treatment of hiccups. The treatment can also be used to relieve asthma, relax bronchial muscles, relieve exercise induced bronchospasm, and relieve bronchial cavity congestion. Relief of headaches can be achieved including migrane, tension and muscular. Relief of vascular spasms can also be achieved. The treatment can also be used to relax intestinal muscle spasms including providing relief of diarrhea.

Prevention and retardation of disuse atrophy can also be accomplished, for example treatment of damage of the thigh hamstring. Similarly, the treatment can be used to correct muscle weakness, increase muscle strength and improve muscle tone.

The present process is also useful for muscle re-education, for example correction of muscle weakness, increasing muscle tone and increasing muscle strength. Application of the periodic-exponential signal can be useful in correcting certain vision system defects by balancing the various muscles associated with the eyeball. The method can be used to treat scoliosis; reduce fatty tissue; and reduce pain, specifically but not limited to lower back pain. Cosmetic body alteration can be accomplished including but not limited to face lift, breast toning, buttock toning and lifting (tucking). The process can also be used to treat hernias (hiatal).

Application of the above-described signal can also be used to reduce stress. The instant process can also be used to provide immediate post-surgical stimulation of calf muscle to prevent venous thrombosis.

Local blood circulation can also be increased through use of the instant treatment. The increase in blood circulation can be beneficial in the treatment of (a) treatment of bone fractures to facilitate mending, (b) treatment of dislocations in any joints, (c) accelerated healing of damaged tissue, and (d) accelerated healing of spinal injuries.

In the treatment of a patient for muscle spasms, the muscle which is in spasm should be determined. Preferably, treatment is effected along the longitudinal axis of the muscle. Preferably a pad is placed at each end of the muscle along the longitudinal axis of the muscle with the muscle itself between the pads. If the muscle being treated is a frontal muscle, then the pad should be placed on the frontal part of the body. If a dorsal or posterior muscle is involved, then the pads should be placed on the dorsal part of the body. If it is not possible to treat longitudinally, transverse treatment can be effective. In this case, the pads are placed perpendicular to the longitudinal axis of the muscle being treated. For example, if hiccups are being treated, transverse stimulation of the diaphragm is preferred. One pad can be placed anterior just below the sternum. The other pad can be placed on the body posterior substantially opposite to the first pad.

The same method of treatment is preferred for preventing a retarding disuse atrophy. Two pad pairs can be used simultaneously to provide more time-effective treatment.

To increase local blood circulation, the treatment region must be determined. If the region is in a limb, treatment is applied transversely by placing a pair of pads so that the region to be treated lies between them. For example, if a knee is being treated, one pad is placed on the inside of the knee while the other pad is placed on the outside of the knee. If the region to be treated is in the body, transverse treatment is similarly preferred, with one pad being paced on the front portion of the body and the other pad placed on the back part of the body. Once again, two pad pairs can be used for more efficient time utilization.

To re-educate muscles, the muscles or muscle groups to be treated should be determined. The same procedure is followed as in treating muscle spasms. Two pad pairs can be used. It is preferred to use continuous-on treatment for the desired period to maximize effect.

In the treatment of calf muscles to prevent venous thrombosis, transverse treatment is preferred. Both pads are preferably placed on the mid-calf with one pad on the inside of the leg and the other on the outside. Optionally, both legs can be treated simultaneously.

The treatment for maintaining an increase in the range of motion involves determining which joint and associated muscle groups are to be treated. Generally, the preferred treatment is transverse across the joint being treated. If the joint is the knee, ankle or elbow, one pad is placed on the inside of the joint with the other pad being placed on the outside relative to the body. If edema is present, a first pad should be placed on the edema with the second pad diametrically opposed thereto. If the joint being treated is the shoulder, wrist, knuckle or finger joints, preferably one pad is placed on the front with the other pad placed on the back of the joint. The foot and toe joints are treated by placing one pad on the top of the joint with the other pad beneath the joint. In the treatment of a hip joint, a remote treatment technique is used. The pads are placed over the posterior ilium slightly above the gluteal maximum. When the region being treated is the back for limited body rotation, stiff neck, limited anterior-posterior bending motion, etc., the preferred treatment is longitudinal in the muscle groups running up and down the left and right sides of the spine. The exact pad placement is determined in a manner similar to that used for muscle spasms.

In the treatment of ulcers, specifically, but not limited to peptic and gastric, the preferred method of treatment is to place the pads transverse. After determining the location of the pain, one pad is placed over the point of pain on the anterior of the body and the other pad is placed on the posterior surface of the body. Preferably, neither pad is inferior (below) or superior (above) the other. Preferably a twenty minute treatment is used at maximum amplitude settings consistent with patient comfort.

The general treatment technique for viral caused diseases is by the transverse stimulation of the lymph node area in the neck and the spleen. Preferably, the pads are placed anterior and posterior to the organ being treated. However, if the throat is being treated, the pads can be placed in lateral positions on the left and right side of the throat. Normally, a twenty minute treatment is used at maximum amplitude setting consistent with patient comfort. The optimal treatment period is three consecutive days.

Certain vision system defects can be corrected by balancing the relative strength of various muscles associated with the eyeball. In the treatment, one pad pair is used for treatment of a single eye. It is preferred that only one eye be treated at a time. This treatment technique involves "indirect" stimulation to the intrinsic ciliary muscle since neither longitudinal nor transverse stimulation is possible. It is expected that miniaturized pads on LOW power settings are required. The amplitude should be adjusted only to the very low edge of patient awareness. The treatment time should be limited to no more than five minutes. Total treatment time varies greatly from patient to patient depending on the nature of the condition and its severity.

In using the instant process to selectively block plasma kinins from its receptor sites, in particular bradykinin, any pad placement can be used. This effect occurs quickly with upper comfort range power settings. The effects appear to be long term in nature. This effect appears to be directly related to the reduction of inflammation and to the reduction of trauma induced edema.

The preferred means for applying the periodic-exponential signal to a patient and the proper placement of the application means on the patient can be readily determined. The proper placement of the application means for the treatment of other afflictions can be readily accomplished to effect the most efficient treatment. As discussed hereinabove, the initial placement will depend upon the location of the afflictions with transverse placement of the application means being initially tried.

The foregoing description of the invention has been presented for purposes of illustration and description. Further, the description is not intended to limit the invention to the form disclosed therein. Consequently, variations and modifications commensurate with the above teachings, and the skill or knowledge in the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternative embodiments to the extent permitted by the prior art.

What is claimed is:

1. A method for treating a symptom associated with injured tissue in a region of a patient, comprising:
   providing a first periodic-exponential signal to the region of the patient;
   wherein a second periodic-exponential signal having a frequency between about 1000 Hz and 100,000 Hz is provided to the region of the patient.

2. The method of claim 1 wherein said second periodic-exponential signal is exponentially amplitude modulated.

3. The method of claim 1 wherein said second periodic-exponential signal is a double-exponential signal.

4. The method of claim 1 wherein the second periodic-exponential signal has a substantially constant peak amplitude.

5. The method of claim 1 wherein said second periodic-exponential signal is clipped.

6. The method of claim 1 wherein said first periodic-exponential signal has a frequency between about 0 Hz and 1000 Hz.

7. A method for treating a symptom associated with injured tissue in a region of a patient, comprising: providing to the region of the patient (a) a first periodic, double-exponential signal having a frequency between about 0 Hz and 1000 Hz and (b) a second periodic, double-exponential signal having a frequency between about 1000 Hz and 100,000 Hz.

8. The method of claim 7 wherein said second periodic, double-exponential signal is exponentially amplitude modulated.

9. The method of claim 7 wherein a portion of said second periodic, double-exponential signal has a substantially constant peak amplitude.

10. The method of claim 7 wherein said second periodic, double-exponential signal is clipped.

11. The method of claim 7 wherein the symptom is inflammation.

12. A method for treating symptoms associated with injured tissue in a region of a patient comprising:
   a) providing a first periodic-exponential signal;
   b) providing a second periodic-exponential signal having a frequency between 1000 Hz and 100,000 Hz;
   c) summing said first and second signals to produce a sum signal; and
   d) applying said sum signal to the region of the patient.

13. The method of claim 12, wherein:
   at least one of said first signal and said second signal is a double-exponential signal.

14. The method of claim 12 wherein:
   at least one of said first signal and said second signal has a substantially constant peak amplitude.

15. The method of claim 12 wherein said second signal is exponentially amplitude modulated.

16. The method of claim 12 wherein: p1 said first signal is clipped.

17. A method for treating symptoms associated with injured tissue in a region of a patient, comprising:
   a) providing a first periodic-exponential signal;
   b) providing a second periodic-exponential signal;
   c) summing said first and second signals to produce a sum signal; and
   d) applying said sum signal to the region of the patient;
   wherein said first signal is blanked when a pulse associated with said second signal is present.

18. A method for treating symptoms associated with injured tissue in a region of a patient comprising:
   a) providing a first periodic-exponential signal;
   b) providing a second periodic-exponential signal;
   c) summing said first and second signals to produce a sum signal; and
   d) applying said sum signal to the region of the patient;
   wherein said first and second signals are each double-exponential signals;
   wherein said first signal is clipped.

19. A method for treating a symptom associated with injured tissue in a region of a patient; comprising:
   a) providing a first periodic-exponential signal;
   b) providing a second periodic-exponential signal;
   c) summing said first and second signals to produce a sum signal; and
   d) applying said sum signal to the region of the patient;
   wherein said symptom is inflammation.

20. A method for improving the relative strength of muscles associated with the eyeball, said method comprising:

providing a signal to a selected group of said muscles;

wherein said signal includes a first portion having a first frequency and a second portion having a second frequency that is different than said first frequency;

wherein said first portion is substantially blanked when at least a portion of a pulse associated with said second portion is present.

21. A method for improving the relative strength of muscles associated with the eyeball, said method comprising:

providing a first periodic-exponential signal to a selected group of said muscles, wherein said first periodic-exponential signal has a frequency between about 0 Hz and 1000 Hz and a second periodic-exponential signal having a frequency between about 1000 Hz and 100,000 Hz is provided to said group of muscles.

22. The method of claim 21 wherein said second periodic-exponential signal is a double-exponential signal and is exponentially amplitude modulated.

23. A method for treating an ulcer said method comprising providing a first periodic-exponential signal to said ulcer.

24. A method for treating an ulcer, said method comprising:

providing a first periodic-exponential signal to said ulcer, wherein said first periodic-exponential signal is a double-exponential signal having a frequency between about 0 Hz and 1000 Hz and a second periodic-exponential signal having a frequency between about 1000 Hz and 100,000 Hz is provided to said ulcer.

25. The method of claim 24 wherein said second periodic-exponential signal is a double-exponential signal and is exponentially amplitude modulated.

26. A method for treating a viral infection in a patient said method comprising providing a first periodic-exponential signal to the infected region of the patient.

27. A method for treating a viral infection in a patient, said method comprising:

providing a first periodic-exponential signal to the infected region of the patient, wherein said first periodic-exponential signal is a double-exponential signal having a frequency between about 0 Hz and 1000 Hz and a second periodic-exponential signal having a frequency between about 1000 Hz and 1100,000 Hz is provided to said region.

28. The method of claim 27 wherein said second periodic-exponential signal is a double-exponential signal and is exponentially amplitude modulated.

29. A method for blocking a plasma kinin from acceptor sites located in injured tissue, said method comprising:

providing a first periodic-exponential signal to the injured tissue.

30. The method of claim 29 wherein said plasma kinin is a bradykinin.

31. A method for blocking a plasma kinin from acceptor sites located in injured tissue, said method comprising:

providing a first periodic-exponential signal to the injured tissue, wherein said first periodic-exponential signal is a double-exponential signal having a frequency between about 0 Hz and 1000 Hz and a second periodic-exponential signal having a frequency between about 1000 Hz and 100,000 Hz is provided to said group of muscles.

32. The method of claim 31 wherein said second periodic-exponential signal is a double-exponential signal and is exponentially amplitude modulated.

33. A method for treating a symptom associated with injured tissue in a region of a patient, comprising:

providing a signal to the region of said patient;

wherein said signal includes a first portion with a first frequency and a second portion with a second frequency that is different than said first frequency;

wherein said first portion is substantially blanked when at least a portion of a pulse associated with said second portion is present;

wherein said second portion of said signal has a frequency between about 0 Hz and 1000 Hz;

wherein at least one portion of said first portion and said second portion includes an exponential signal.

* * * * *